(12) United States Patent
Xu et al.

(10) Patent No.: US 8,185,179 B2
(45) Date of Patent: May 22, 2012

(54) FINGERTIP OXIMETER AND A METHOD FOR OBSERVING A MEASUREMENT RESULT THEREON

(75) Inventors: Feng Xu, Beijing (CN); Shuhai Liu, Beijing (CN)

(73) Assignee: Beijing Choice Electronic Technology, Co., Ltd., Beijing (CN)

( * ) Notice: Subject to any disclaimer, the term of this patent is extended or adjusted under 35 U.S.C. 154(b) by 1113 days.

(21) Appl. No.: 12/065,797

(22) PCT Filed: Mar. 12, 2007

(86) PCT No.: PCT/CN2007/000791
§ 371 (c)(1),
(2), (4) Date: Mar. 5, 2008

(87) PCT Pub. No.: WO2008/019548
PCT Pub. Date: Feb. 21, 2008

(65) Prior Publication Data
US 2008/0242959 A1 Oct. 2, 2008

(30) Foreign Application Priority Data
Aug. 7, 2006 (CN) .......................... 2006 1 0089152

(51) Int. Cl.
*A61B 5/1455* (2006.01)
(52) U.S. Cl. ...................................... 600/323

(58) Field of Classification Search ............... 600/310, 600/322, 323, 300; 345/418, 168
See application file for complete search history.

(56) References Cited

U.S. PATENT DOCUMENTS

| 5,490,523 | A  | * | 2/1996  | Isaacson et al. ............ 600/323 |
| 6,018,673 | A  | * | 1/2000  | Chin et al. ................. 600/322 |
| 6,571,114 | B1 | * | 5/2003  | Koike et al. ................ 600/323 |
| 6,654,621 | B2 | * | 11/2003 | Palatnik et al. ............. 600/322 |
| 2002/0161291 | A1 |   | 10/2002 | Kianl et al. |
| 2005/0004487 | A1 |   | 1/2005  | Ishida et al. |

FOREIGN PATENT DOCUMENTS

| JP | 04134493 A   | 5/1992 |
| JP | 2005221660 A | 8/2005 |
| WO | 0215781 A    | 2/2002 |

* cited by examiner

*Primary Examiner* — Eric Winakur
(74) *Attorney, Agent, or Firm* — Finnegan, Henderson, Farabow, Garrett & Dunner, LLP

(57) ABSTRACT

There is provided a fingertip oximeter that has a plurality of display modes which are presented sequentially in a circulating way, allowing users to easily observe a measurement result from any of surrounding directions. The present invention makes users to be able to observe a measurement result of the fingertip oximeter from any of surrounding directions, without the need of bending his/her finger. Thus, any partial occlusion of the arterial blood capillary can be avoided, so that strength of the pulse will not decrease, and strength of the signal will not be affected. As a result, the precision of the measurement is improved.

4 Claims, 3 Drawing Sheets

FINGERTIP OXIMETER AND A METHOD FOR OBSERVING A MEASUREMENT RESULT THEREON

FIELD OF THE PRESENT INVENTION

The present invention relates to a fingertip oximeter, and more particularly, to a fingertip oximeter allowing observation of a measurement result displayed thereon from any of surrounding directions.

In another aspect, the present invention relates to a method for allowing observation of a measurement result of the fingertip oximeter from any of surrounding directions.

In the third aspect, the present invention relates to a fingertip oximeter that reports a measurement result through a voice, informing the user and others nearby of the result.

BACKGROUND OF THE PRESENT INVENTION

The fingertip oximeter, widely used for measuring the oxyhemoglobin and pulse, employs a non-invasive measurement technology.

The fingertip oximeter runs in such a way that it determines the oxyhemoglobins number and pulse rate by measuring the absorption rate for a selected wavelength of light wave. In particular, a beam of light from a photoelectric light emitter is arranged to pass through the organism tissue of the user, and is converted to an electrical signal after being detected by a light receiver. Thereby, an oxygen saturation level (i.e. SpO2) of arterial blood flowing through the finger of the user is obtained and presented on a display of the oximeter.

In the prior art, however, the user can observe a measurement result in only one direction. When observing the result, the user has to bend his/her finger to properly observe the displayed information if it is not easy to read. But bending the finger may lead to partial occlusion of arterial blood capillary so that the strength of pulse will decrease and the strength of signal is weakened. As a result, the precision of measurement falls.

SUMMARY OF THE PRESENT INVENTION

The object of the present invention is to provide a fingertip oximeter allowing observation of a measurement result thereon from any of surrounding directions, in which when observing the result, the user does not to bend his/her finger to properly observe the displayed information even if it is not easy to read, so as to avoid the partial occlusion of arterial blood capillary, thus to prevent from any decrease of the strength of pulse and further prevent from any decrease of the strength of signal, as a result, the precision of measurement can be improved.

Another object of the present invention is to provide a method for allowing observation of a measurement result of a fingertip oximeter from any of surrounding directions.

The further object of the present invention is to provide a fingertip oximeter that can report a measurement result through a voice, informing the user and others nearby of the measurement result.

Thus, according to the first aspect of the present invention, there is provided a fingertip oximeter characterized in that it has a plurality of display modes which are sequentially presented in a circulating way, allowing a user to easily observe a measurement result from any of surrounding directions.

Preferably, one of the display modes is switched to the next by pressing a button manually, or they are switched automatically.

Preferably, the display mode refers to a pattern of presenting a measurement result, or a pattern of presenting a combination of a heading and a measurement result; and the heading is presented in an upright standing or upside-down standing way.

Preferably, the measurement result comprises a measurement parameter, a measurement parameter and a pulse column, or a measurement parameter and a waveform; the measurement parameter can be presented in a landscape upright standing, a portrait right laying way, a landscape upside-down standing way, or a portrait left laying way.

Preferably, the fingertip oximeter comprises a signal drive unit, a signal acquisition & amplification unit, a power supply unit for supplying power to the fingertip oximeter, buttons, a central processing unit, and a display, in which the buttons are adapted to input an instruction for updating a display mode of the fingertip oximeter; the central processing unit is adapted to determine whether any button is pressed down, upon such an operation is detected, to set a new display mode and update the display mode in use with the new one, and to transmit a signal regarding the new display mode to the display; and the display is adapted to receive the signal regarding the new display mode from the central processing unit, and present the measurement result in the new display mode.

Preferably, the central processing unit at least comprises a press scan unit, a switching & setting unit, and a display update unit, in which the press scan unit is adapted to determine whether any button is pressed down, and upon such an operation is detected, to transmit a first signal regarding the operation to the switching & setting unit; the switching & setting unit is adapted to receive the first signal from the press scan unit, set a new display mode in consideration of the display mode in use, and transmit a second signal regarding the new display mode to which the display mode in use is to be switched to the display update unit; and the display update unit is adapted to receive the second signal from the switching & setting unit, update the display mode in use, and transmit a third signal regarding the new display mode to the display.

According to the second aspect of the present invention, there is provided a method for allowing observation of a measurement result of a fingertip oximeter from any of surrounding directions, characterized in that the method comprises the following steps of: 1) inputting an instruction for updating a display mode of the fingertip oximeter in use; 2) switching and updating the display mode in use to a new display mode, and transmitting a signal regarding the new display mode to a display after the instruction is detected; and 3) displaying a measurement result in the new display mode after the display receives the signal on updating the display mode in use.

Preferably, the step 2) further comprises the sub-steps of detecting the instruction for updating the display mode in use; setting a new display mode to which the display mode in use is to be switched; and updating the display mode in use with the new display mode, and transmitting a signal regarding the new display mode to a display.

Preferably, the display mode refers to a pattern of presenting a measurement result, or a pattern of presenting a combination of a heading and a measurement result; and the heading is presented in an upright standing or upside-down standing way.

Preferably, the measurement result comprises a measurement parameter, a measurement parameter and a pulse column, or a measurement parameter and a waveform; the measurement parameter is presented in a landscape upright standing, a portrait right laying way, a landscape upside-down standing way, or a portrait left laying way.

According to the third aspect of the present invention, there is provided a fingertip oximeter that can reports a measurement result through a voice to the user and others nearby.

According to the present invention, the user can easily observe a measurement result of the fingertip oximeter from any of surrounding directions, without the need of bending his/her finger when observing the measurement result, which avoids partial occlusion of arterial blood capillary due to bended finger, thus, prevents from decrease of the strength of pulse, so does not weaken the strength of signal, so as to improve the precision of measurement.

DETAILED DESCRIPTION OF THE PREFERRED EMBODIMENTS

The embodiments of the present invention are described in detail in combination with the drawings below.

According to an embodiment of the present invention, the display of the oximeter is an organic light emitting display (OLED), which is a 64×128 dot array monochrome display. The color of the first 16 rows of the display is configured as yellow, while that of the other 48 rows is configured as blue in the embodiment. But different displays and displaying patterns may be applied.

In practice, the display mode usually refers to a pattern in which a measurement result or a combination of a heading and a measurement result is presented. The way in which the heading is presented could be set to upright standing or upside-down standing as required. Landscape or portrait appearance is also available.

The measurement result comprises a measurement parameter, a measurement parameter and a pulse column, or a measurement parameter and a waveform. The way in which the measurement parameter is presented includes landscape upright standing, portrait right laying, landscape upside-down standing, or portrait left laying. The way in which the pulse column is presented includes the pulse column's left display, center display, or right display. The way in which the waveform is presented could be solid standing or outlined standing as required. Landscape or portrait appearance is also available.

The above described display options can be used in combination according to the situation of usage.

In this embodiment, the display mode refers to the way in which the heading and the measurement result are presented.

In this embodiment, the display screen is divided into a heading area and a parameter area. The heading area occupies the top 16 rows as a yellow block, while the parameter area fills the following 48 rows as a blue block. Characters in the heading area can only be displayed with a certain height, and in an upright standing or upside-down standing appearance. The height of characters in the parameter area is not fixed. Some graphics or waveforms can also be displayed in the parameter area. In this area, characters can be displayed in an upright standing, an upside-down standing, a left laying, or a right laying appearance.

Referring to FIG. 1A to FIG. 1F, six display modes are illustrated in an embodiment of the present invention.

Figure 1A:
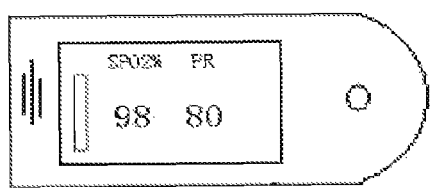
FIG. 1A to FIG. 1F are schematic views of different display modes of the oximeter according to one embodiment of the present invention.

Referring to FIG. 1A, in Mode 0, the heading (SPO2% and PR) is displayed in a landscape upright standing way, measurement parameters (98 and 80) are displayed in a landscape upright standing way, and a pulse column is displayed in a landscape left standing way. Here, the pulse column is adapted to indicate strength of pulse.

Figure 1B:
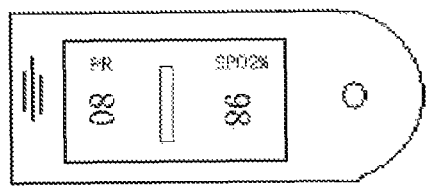

Referring to FIG. 1B, in Mode 1, the heading (PR and SPO2%), measurement parameters (80 and 98), and the pulse column are respectively displayed in a portrait upright standing way, a portrait right laying way, and a centered standing way.

Figure 1C:
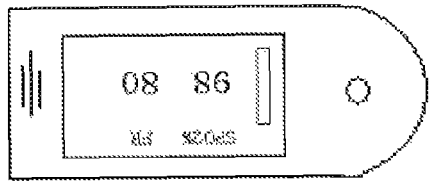

Referring to FIG. 1C, in Mode 2, the heading (SPO2% and PR), measurement parameters (98 and 80), and the pulse column are respectively displayed in a landscape upside-down standing way, a landscape upside-down standing way, and a right standing way.

Figure 1D:
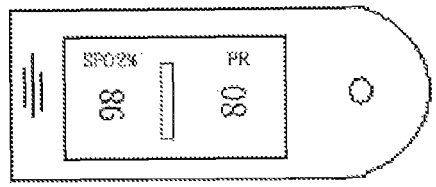

Referring to FIG. 1D, in Mode 3, the heading (SPO2% and PR) is displayed in a landscape upright standing way, measurement parameters (98 and 80) are displayed in a portrait left laying way, and the pulse column is displayed in a centered standing way.

Figure 1E:
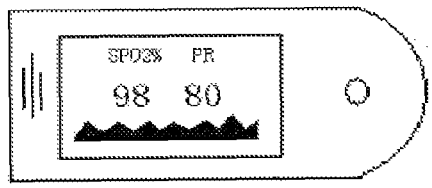

Referring to FIG. 1E, in Mode 4, the heading (SPO2% and PR) is displayed in a landscape upright standing way, measurement parameters (98 and 80) are displayed in a landscape upright standing way, and a landscape solid waveform is displayed.

Figure 1F:
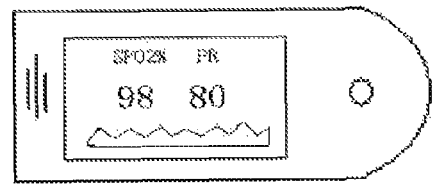

Referring to FIG. 1F, in Mode 5, the heading (SPO2% and PR) is displayed in a landscape upright standing way, measurement parameters (98 and 80) are displayed in a landscape upright standing way, and a landscape outlined waveform is displayed.

When the fingertip oximeter is powered on and initialized, the operating modes and parameters of the display are set up. At the beginning of measurement, the display mode is set to 0 initially.

Figure 2:
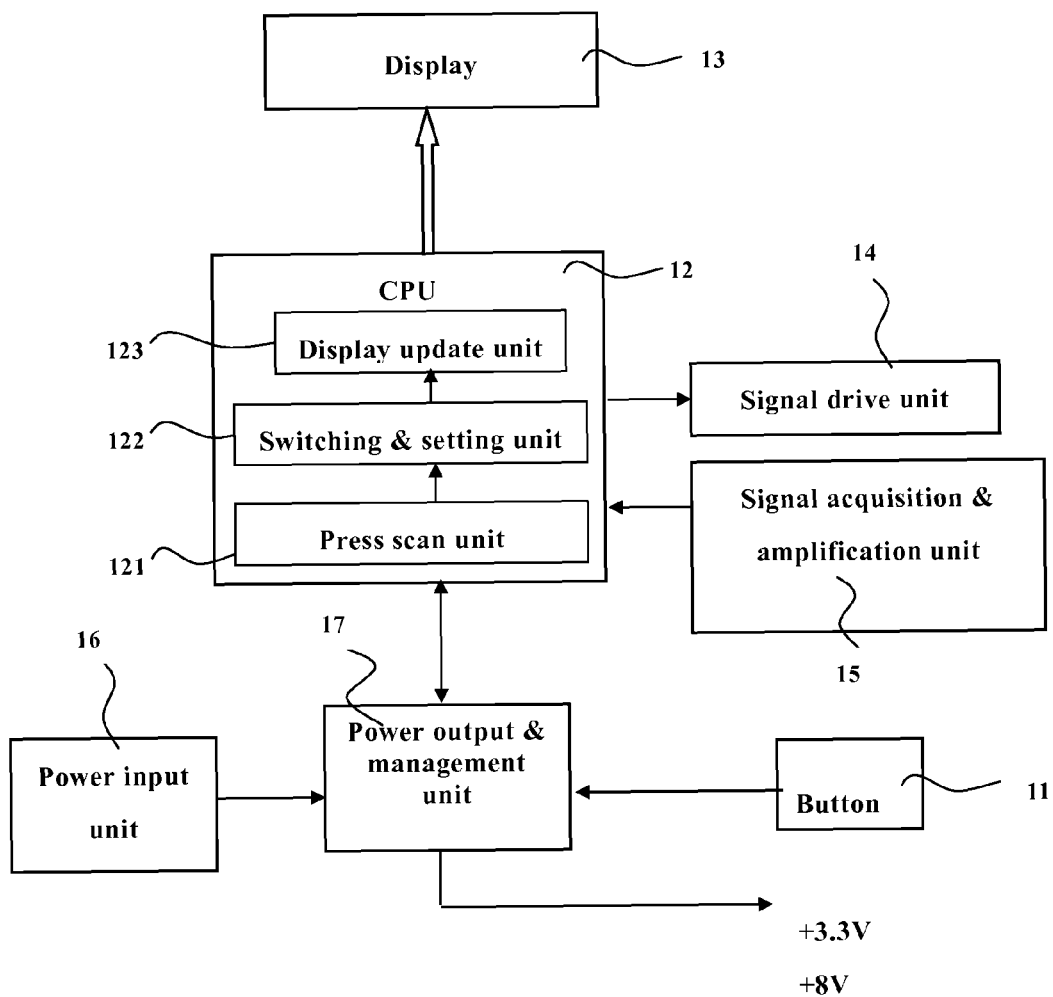
FIG. 2 is a block diagram of the oximeter according to one embodiment of the present invention.
Figure 3:
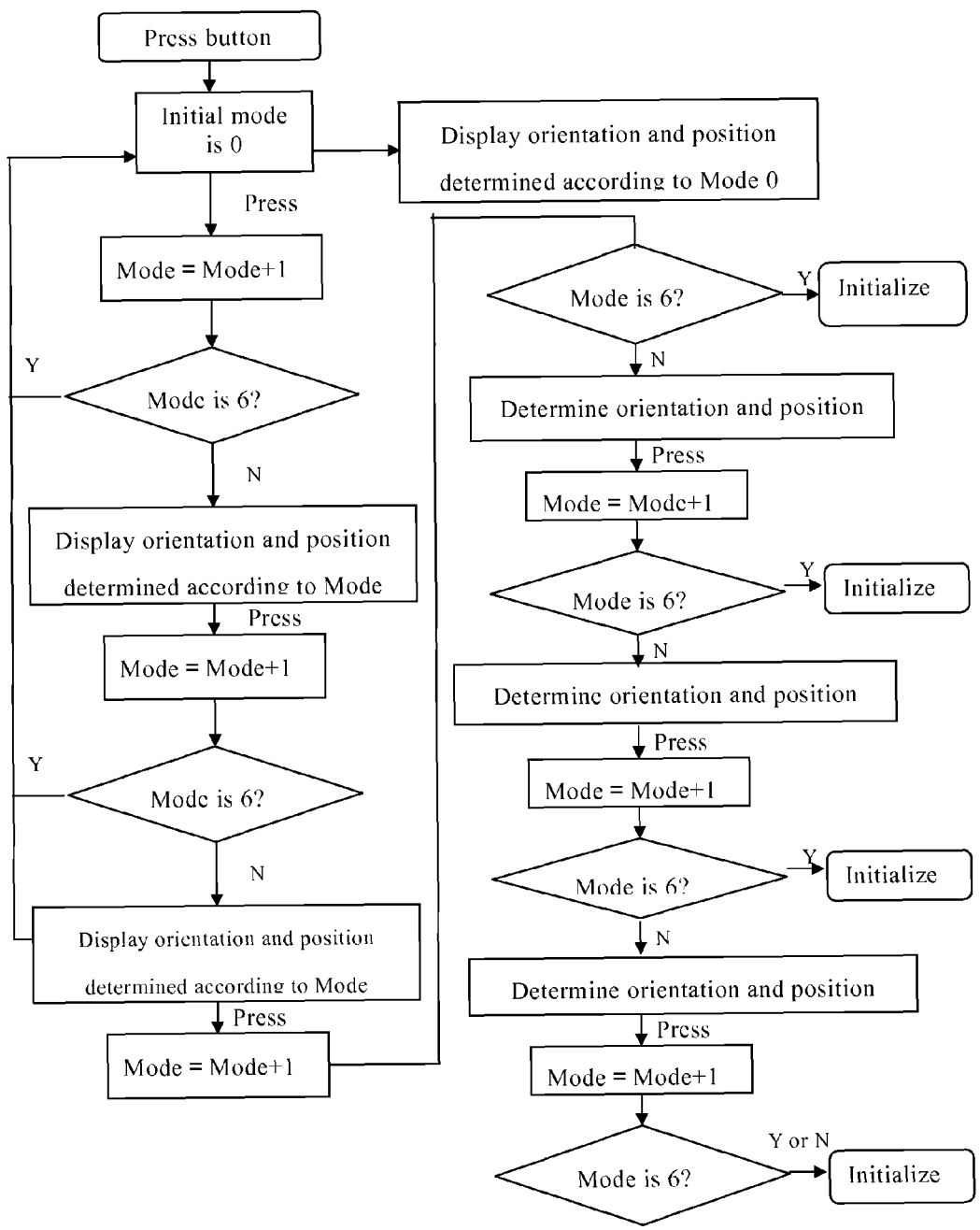
FIG. 3 is a flow diagram of updating a display mode of the oximeter according to one embodiment of the present invention.

Referring to FIG. 2, according to an embodiment of the present invention, as the central processing unit (CPU) 12 detects that the button 11 is pressed down for one time, the display mode is updated once. When the button 11 is pressed down again, the display mode is also updated again. Each time the button 11 is pressed down, the display mode is switched from Mode 0 to Mode 5 one by one and then to go back to Mode 0 to continue the next cycle again. Therefore, the measurement result can be easily observed from any of surrounding directions.

These six display modes form only one embodiment of the present invention. Other display modes are also possible in practice according to the present invention. For example, the central processing unit 12 can be configured to automatically update the display mode sequentially from Mode 0 to Mode 5 one by one and then back to Mode 0 to repeat the next cycle at a specific interval, so that the measurement result of the fingertip oximeter can be easily observed from any of surrounding directions. The interval can be predetermined as required to make the display cycle time of the modes faster or slower.

In addition, according to another embodiment of the present invention, the fingertip oximeter can be integrated with the voice making technology from prior art, speaking any number corresponding to the measurement result, to automatically report the measurement result through a voice. Consequently, the user and others nearby can be informed of that result directly, making the users more conveniently to use the fingertip oximeter.

Referring to FIG. 2, the fingertip oximeter based on one embodiment of the present invention comprises a signal drive unit 14, a signal acquisition & amplification unit 15, a power supply units 16 and 17 for supplying power to the fingertip oximeter, a central processing unit 12, a display 13, and buttons 11. The buttons 11 for inputting an instruction to update a display mode of the oximeter are connected with the power supply unit for activating the power supply unit to supply power to the oximeter. The central processing unit 12 is adapted to determine whether any button 11 is pressed down, set a new display mode to which the display mode in use is to be switched in response to pressing-down of the button 11, update the display mode in use, and transmit a signal regarding the new display mode to the display 13. The display 13 is adapted to receive the signal regarding the new display mode from the central processing unit 12, and display the measurement result in the updated display mode.

According to one embodiment of the present invention, the signal drive unit 14 and the signal acquisition & amplification unit 15 can be made use of prior art.

Referring to FIG. 2, the central processing unit 12 at least comprises a press scan unit 121, a switching & setting unit 122, and a display update unit 123. The press scan unit 121 is adapted to determine whether any button 11 is pressed down, and transmit a first signal regarding pressing-down of the button 11 to the switching & setting unit 122 in response to pressing-down of the button 11. The switching & setting unit 122 is adapted to receive the first signal from the press scan unit 121, set a new display mode to which the display mode in use is to be switched, and transmit a second signal regarding the new display mode to the display update unit 123. The display update unit 123 is adapted to receive the second signal regarding the new display mode from the switching & setting unit 122, update the display mode in use with the new display mode, and transmit a third signal regarding the new display mode to the display 13.

The signal drive unit 14, under control of the central processing unit 12, is adapted to make a light emitter emit a beam of light. The signal acquisition & amplification unit 15 is adapted to receive the light passing through the measured tissue, convert it to an electric signal, and transmit the electric signal to the central processing unit 12.

In this embodiment, the power supply unit includes a power input unit 16 and a power output & management unit 17. The button 11 and the power input unit 16 are connected with the power output & management unit 17 respectively.

According to one embodiment of the present invention, the central processing unit 12 makes use of a C8051F007 chip available from CYGNAL Corporation, which has a 2304-byte data memory, a 32K FLASH memory, a 4-channel 12-bit A/D (Analog/Digital) converter, a 2-channel 12-bit D/A (Digital/Analog) converter, 2 comparators, a on-board 2.4V voltage reference, a on-board clock source, and a 4-channel 16-bit counter/timer.

According to one embodiment of the present invention, the display 13 is an OLED for presenting the measurement result. The I/O (Input/Output) interface of the central processing unit 12 is driven directly.

In this embodiment, the power input unit 16 consists of two AAA alkaline batteries or rechargeable batteries, providing a voltage of 2.3 to 3.3V.

According to one embodiment of the present invention, the output of the power output & management unit 17 is +3.3V and +8V. When turning off, the power input can be disconnected so that the output of the power supply becomes 0V.

The power output of 2.3V to 3.3V is converted to a 3.3V and 8V output through a MT1860 power chip. The maximum power output is 400 mA, with a frequency of 1 MHz in PWM (Pulse Width Modulation) mode.

The power management is carried out by using the button or I/O output. When the button 11 is pressed down, the voltage output is +3.3V. The central processing unit 12 takes over power control and outputs a voltage of +8V if it detects that the button 11 is pressed down.

The power supply works as usual after releasing the button 11. If the master chip cannot detect any data for 8 seconds, the system is shut down, being in the sate of turning off.

If it detects that the voltage input is as low as lower than +2.7V, then a low-battery-voltage alert is displayed to prevent the input power supply from damage.

After the button 11 is pressed down, a low level signal or a high level signal is generated, and an interrupt is further made, so the central processing unit 12 is aware of the fact that the button 11 is pressing down in this way. The central processing unit 12 then sets a new display mode and switches current display mode to the new display mode.

The central processing unit (CPU) 12 may make use of a chip other than that described above. In addition, the analog comparison input involved in this embodiment for transmitting information regarding pressing-down the button 11 to the central processing unit 12 can be replaced with an I/O interface input or an interrupt interface input.

In another aspect of the present invention, there is provided a method for observing a measurement result of a fingertip oximeter, comprising the following steps of: step 1) inputting an instruction for updating a display mode of the fingertip oximeter in use; step 2) switching and updating the display mode in use and transmit a signal regarding a new display mode to a display of the fingertip oximeter after detecting the instruction; and step 3) presenting a measurement result in the updated new display mode after the display receives the signal regarding the new display mode.

Preferably, step 2) further comprises the following sub-steps of detecting the instruction for updating the display mode of the fingertip oximeter in use, setting a new display mode to which the display mode in use is to be switched; updating the display mode in use with the new display mode, and transmitting a signal regarding the new display mode to the display.

Now, a method for observing a measurement result of the fingertip oximeter from any of surrounding directions is described according to one embodiment the present invention. The method comprises such steps that step 1) the user inputs an instruction for updating a display mode of the fingertip oximeter in use by pressing the button 11 down; step 2) the central processing unit 12 sets a new display mode to which the display mode in use is to be switched, updates the display mode in use with the new display mode, and transmits a signal regarding the new display mode to the display 13 after detecting pressing-down of the button 11; and step 3) the display 13 receives the signal regarding the new display mode to be presented from the central processing unit 12, and presents a measurement result in the updated new mode.

Preferably, step 2) further comprises such sub-steps that the press scan unit 121 determines whether the button 11 is pressed down, and transmits a first signal regarding pressing-down of the button 11 to the switching & setting unit 122 if it detects that the button 11 is pressed down; the switching & setting unit 122 receives the first signal from the press scan unit 121, and sets a new display mode to which the display mode in use is to be switched, and transmits a second signal regarding the new display mode to the display update unit 123; and the display update unit 123 receives the second signal from the switching & setting unit 122, updates the display mode in use, and transmits a third signal regarding the new display mode to the display 13.

Referring to FIG. 3 and FIGS. 1A to 1F, the method is further described below with the example of the foregoing six display modes.

When the fingertip oximeter is in off status, it will be turned on if the button 11 is pressed down for the first time. And then, the fingertip oximeter is automatically powered on and initialized. The initial display mode is set to Mode 0.

From then on, once the central processing unit 12 detects that the button 11 is pressed down, the display mode will be updated. If the button 11 is pressed down again, the display mode is switched to another new display mode. In this way, the display mode is switched from Mode 0 to Mode 5 one by one and return the initial Mode 0 again, and then to be in the next cycle. Thus, the measurement result can be easily observed from any of surrounding directions.

In particular, the press scan unit 121 of the central processing unit 12 determines whether the button 11 is pressed down at a specific interval. If the button 11 has not yet been pressed down, the display update unit 123 and a blood oxygen parameters & waveform processing unit will continue to try to detect it again and again in the same way as that of prior art. Once it is detected that the button 11 is pressed down, a first signal regarding its pressing-down is transmitted to the switching & setting unit 122 to be processed; the switching & setting unit 122 receives the first signal detected by the press scan unit 121, performs a specific counting operation, filters noise signals resulted from the button's trembling, sets a new display mode (Mode 1) to replace the original display mode (Mode 0), initializes the screen of the display with the new display mode, and transmits a second signal regarding the new display mode (Mode 1) to the display update unit 123; the display update unit 123 checks the display update flag at a specific interval, and displays a measurement result on the display 13 in the new display mode (Mode 1) if any parameters and waveforms are updated.

In this embodiment, the display mode is changed to Mode 1 if the button 11 is pressed down for the first time, to Mode 2 if the button 11 is pressed down for the second time, and so on.

The changing sequence of display modes is not fixed. The sequence of display modes can be adjusted to satisfy specific needs. In addition, other display modes can be added to make a comprehensive set of display modes.

With the present invention, the user can easily observe a measurement result from any of surrounding directions, without the need of bending his/her finger, so the precision of measurement is guaranteed.

All embodiments described above are illustrative, not restrictive for the present invention.

Although the present invention has been described in several embodiments, it will be appreciated by those skilled in the art that the present invention can be modified or improved in these or those ways, without departing from the spirit and scope of the present invention indicated by the appended claims.

The invention claimed is:

1. A fingertip oximeter, comprising:
    a display update unit and display for displaying a measurement result to a user using a plurality of display modes which are configured to be presented one by one in a circulating way, headings and parameters of the measurement result being displayed in different directions for the user to observe from any of surrounding directions without changing the direction of the fingertip oximeter relative to the user; and
    a manually pressing button for updating the display mode in use,
    wherein each display mode divides a screen of the display into a heading area and a parameter area, in which characters in the heading area are presented in an upright standing way or in an upside-down standing way, while the parameter area is provided to show a measurement parameter, or a measurement parameter and a pulse column, or a measurement parameter and a waveform in an upright standing way, in a right laying way, in an upside-down standing way, or in a left laying way,
    wherein the display update unit is configured to generate at least six display modes (Mode 0-Mode 5), wherein:
    in Mode 0, the heading is displayed in a landscape upright standing way, measurement parameters are displayed in a landscape upright standing way, and a pulse column for indicating the strength of pulse is displayed in a landscape left standing way;
    in Mode 1, the heading, measurement parameters, and the pulse column are respectively displayed in a portrait upright standing way, a portrait right laying way, and a centered standing way;
    in Mode 2, the heading, measurement parameters, and the pulse column are respectively displayed in a landscape upside-down standing way, a landscape upside-down standing way, and a right standing way;
    in Mode 3, the heading is displayed in a landscape upright standing way, measurement parameters are displayed in a portrait left laying way, and the pulse column is displayed in a centered standing way;
    in Mode 4, the heading is displayed in a landscape upright standing way, measurement parameters are displayed in a landscape upright standing way, and a landscape solid waveform is displayed; and
    in Mode 5, the heading is displayed in a landscape upright standing way, measurement parameters are displayed in a landscape upright standing way, and a landscape outlined waveform is displayed.

2. A fingertip oximeter according to claim 1, wherein the manually pressing button is configured to receive an instruction for updating the display mode of the fingertip oximeter in use, the fingertip oximeter further comprising:
    a central processing unit which is adapted to determine whether any button is pressed down, upon such an operation being detected, set a new display mode and update the display mode in use with the new one, and transmit a signal regarding the new display mode to the display;
    a signal drive unit which is adapted to make a light emitter emit a beam of light under control of the central processing unit;
    a signal acquisition and amplification unit which is adapted to receive the light passing through the measured tissue, convert it to an electric signal, and transmit the electric signal to the central processing unit; and
    a power supply unit, for supplying power to the fingertip oximeter, which includes a power input unit and a power output and management unit, and the button and the power input unit are connected with the power output and management unit respectively.

3. A fingertip oximeter according to claim 2, wherein the central processing unit at least comprises a press scan unit, a switching and setting unit, and the display update unit, in which the press scan unit is adapted to determine whether any button is pressed down, and upon such an operation is detected, transmit a first signal regarding the operation to the switching and setting unit; and wherein the switching and setting unit is adapted to receive the first signal from the press scan unit, set a new display mode in consideration of the display mode in use, and transmit a second signal regarding the new display mode to which the display mode in use is to be switched to the display update unit, and the display update unit is adapted to receive the second signal from the switching and setting unit, update the display mode in use, and transmit a third signal regarding the new display mode to the display.

4. A method for observing a measurement result on a fingertip oximeter from any of surrounding directions, the fingertip oximeter comprising a central processing unit, a display, a press scan unit, a switching and setting unit, a button, and a display update unit, the method comprising the following steps:

step 1) the user inputs an instruction for updating a display mode of the fingertip oximeter in use by pressing the button down;

step 2) the central processing unit sets a new display mode to which the display mode in use is to be switched, updates the display mode in use with the new display mode, and transmits a signal regarding the new display mode to the display after detecting pressing-down of the button; and step 3) the display receives the signal regarding the new display mode to be presented from the central processing unit, and presents a measurement result in an updated new mode, wherein step 2) further comprises such substeps that the press scan unit determines whether the button is pressed down, and transmits a first signal regarding pressing-down of the button to the switching and setting unit if it detects that the button is pressed down; the switching and setting unit receives the first signal from the press scan unit, and sets a new display mode to which the display mode in use is to be switched, and transmits a second signal regarding the new display mode to the display update unit; and the display update unit receives the second signal from the switching and setting unit, updates the display mode in use, and transmits a third signal regarding the new display mode to the display, wherein the display update unit is configured to generate at least six display modes (Mode 0-Mode 5), wherein:

in Mode 0, the heading is displayed in a landscape upright standing way, measurement parameters are displayed in a landscape upright standing way, and a pulse column for indicating the strength of pulse is displayed in a landscape left standing way;

in Mode 1, the heading, measurement parameters, and the pulse column are respectively displayed in a portrait upright standing way, a portrait right laying way, and a centered standing way;

in Mode 2, the heading, measurement parameters, and the pulse column are respectively displayed in a landscape upside-down standing way, a landscape upside-down standing way, and a right standing way;

in Mode 3, the heading is displayed in a landscape upright standing way, measurement parameters are displayed in a portrait left laying way, and the pulse column is displayed in a centered standing way;

in Mode 4, the heading is displayed in a landscape upright standing way, measurement parameters are displayed in a landscape upright standing way, and a landscape solid waveform is displayed; and in Mode 5, the heading is displayed in a landscape upright standing way, measurement parameters are displayed in a landscape upright standing way, and a landscape outlined waveform is displayed.

* * * * *